US00PP28140P3

(12) United States Plant Patent
Probasco et al.

(10) Patent No.: US PP28,140 P3
(45) Date of Patent: Jun. 27, 2017

(54) HOP PLANT NAMED 'HBC 344'

(50) Latin Name: *Humulus lupulus*
Varietal Denomination: HBC 344

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, LLC., Yakima, WA (US)

( * ) Notice: Subject to any disclaimer, the term of this patent is extended or adjusted under 35 U.S.C. 154(b) by 0 days.

(21) Appl. No.: 14/545,738

(22) Filed: Jun. 11, 2015

(65) Prior Publication Data

US 2016/0278264 P1 Sep. 22, 2016

Related U.S. Application Data

(60) Provisional application No. 62/177,537, filed on Mar. 16, 2015.

(51) Int. Cl.
*A01H 5/00* (2006.01)

(52) U.S. Cl.
USPC ..... Plt./236

(58) Field of Classification Search
USPC ..... Plt./236
CPC ..... A01H 5/00
See application file for complete search history.

(56) References Cited

PUBLICATIONS http://www.bear-flavored.com/2013/06/new-hops-alert-hbc-291-hbc-344-hbc-366.html; Jun. 27, 2013; 3 pages.*

* cited by examiner

*Primary Examiner* — Kent L Bell
(74) *Attorney, Agent, or Firm* — Ballew Law

(57) ABSTRACT

A new hop plant named 'HBC 344' is disclosed. The cones of 'HBC 344' mature in late September, and yields a crop of 1,600 to 2,000 pounds per acre. 'HBC 344' is used for its aromatic quality.

1 Drawing Sheet

Genus and species: *Humulus lupulus*.
Variety denomination: 'HBC 344'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'HBC 344' is a product of a controlled breeding program carried out by the inventors in the Yakima Valley of Washington State. 'HBC 344' was one of several seedlings resulting from a cross made in 2001 of female parent YCR 5 (U.S. Plant Pat. No. 12,404) and male parent YCR 136M not patented. A single plant of 'HBC 344' was selected in 2006, and in 2007 was asexually expanded to 30 plants via softwood cuttings, which were planted in the area of Toppenish, Wash. The plants were observed and evaluated for several years, and in 2010 were expanded for further observation and evaluation in the Topennish, Wash. area. A 1 acre test plot of 'HBC 344' was established in 2011. Throughout several generations of asexual propagation, 'HBC 344' has been observed to retain its distinctive characteristics and remain true to type.

BRIEF DESCRIPTION OF THE PHOTOGRAPH

FIG. 1 illustrates a mature 'HBC 344' hop plant grown on a trellis; and

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2011-2014 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Color Chart.

Ploidy: Diploid.

Use: Brewing.

Plant shoot emergence: Generally, occurs in March of each year, but varies by year.

Harvest date: September 20 to 26 (during 2011 to 2014 growing seasons at Toppenish, Wash.).

Crop yield: 1600 to 2000 pounds per acre.

Disease susceptibility: Susceptible to both powdery mildew and downy mildew.

Hop aroma: A pleasant floral fruity aroma of Juicy Fruit™ and Jolly Rancher™, with complex savory undertones of herbal tea and eucalyptus.

Analytical characteristics:

*Alpha acid* (*as % of cone weight*).—14.2% to 15.5%.
*Beta acid* (*as % of cone weight*).—4.5% to 5.4%.
*Cohumulone* (*as % of alpha acids*).—24.6% to 29.4%.
*Total oil*.—1.0-2.0 ml/100 g.
*Humulene*.—0.88-0.91% of total oils.
*Caryophyllene*.—11.07-16.98% of total oils.
*Myrcene*.—47.88-64.95% of total oils.
*Farnesene*.—0.03-0.06% of total oils.

Bine:

*Color*.—144B.
*Stripe present*.—Yes.
*Stripe color*.—60A.
*Stipule direction*.—Up-forked.
*Stipule color*.—144D.
*Bine internode length*.—150 to 250 mm.
*Bine diameter*.—8.16 mm at nine feet; 5.33 mm at terminal end of eighteen feet.

Laterals:

*Lateral length*.—50 to 150 cm average.
*Lateral diameter*.—3 to 5 mm average diameter at base and 0.5 to 1 mm at terminus.
*Lateral Color*.—144B.
*Lateral stipule color*.—144D.

Leaf:

*Arrangement*.—Opposite.
*Shape*.—Palmately Lobed to Cordate.
*Apex shape*.—Acuminate.
*Base shape*.—Cordate.
*Average length of mature leaf*.—13.37 cm.
*Average width of mature leaf*.—18 cm.
*Color of mature leaf upper surface*.—147A.
*Color of mature leaf lower surface*.—147B.
*Color of immature leaf upper surface*.—147A.
*Color of immature leaf lower surface*.—147B.
*Number of lobes*.—1-5.
*Margin*.—Serrate.
*Serrations per inch*.—4.5.
*Average petiole length* (*mature*).—8.87 cm.
*Average petiole diameter*.—2 to 4 mm at base.
*Petiole color at base*.—144B, 59A.
*Venation*.—Palmate.
*Vein color*.—145C.

Cone:

*Cone shape*.—Ovoid.
*Avg. length*.—3.365 cm.
*Avg. diameter*.—1.64 cm.
*Avg cone weight*.—0.77 mg.
*Bract shape*.—Ovate.
*Bract length*.—7 to 11 mm average.
*Bract width*.—5 to 10 mm average.
*Bract tip color*.—145C.
*Bract base color*.—149D.
*Bract inner surface color*.—145C.
*Bract outer surface color*.—149D.
*Bracteole color*.—149D.
*Bract tip shape*.—Cuspidate.
*Bract tip position*.—Moderately to tightly appressed.
*Bracteole shape*.—Ovate.
*Lupulin glands*.—Moderate to High number of lupulin glands on average per cone.
*Lupulin gland shape*.—Pedunculated oblong polyps.

What is claimed is:

1. A new and distinct Hop plant as illustrated and described herein.

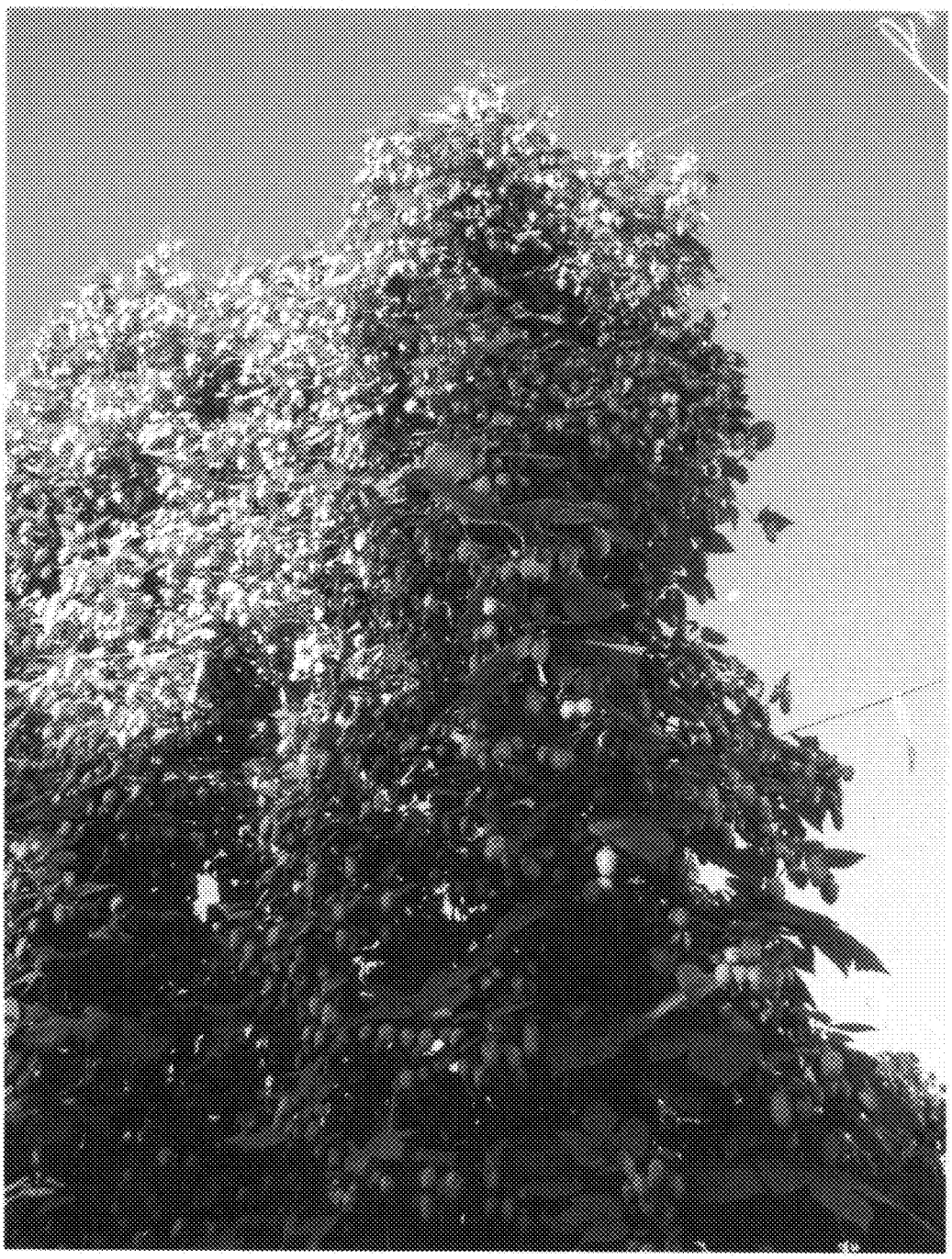

* * * * *